(12) United States Patent
Olson

(10) Patent No.: US 11,730,943 B2
(45) Date of Patent: Aug. 22, 2023

(54) LOW-FRICTION SEALING DEVICES

(71) Applicant: Surmodics, Inc., Eden Prairie, MN (US)

(72) Inventor: Charles Olson, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 272 days.

(21) Appl. No.: 17/007,770

(22) Filed: Aug. 31, 2020

(65) Prior Publication Data

US 2021/0052878 A1 Feb. 25, 2021

Related U.S. Application Data

(63) Continuation of application No. 15/838,677, filed on Dec. 12, 2017, now Pat. No. 10,758,719.
(Continued)

(51) Int. Cl.
| | |
|---|---|
| *A61M 39/06* | (2006.01) |
| *A61B 17/34* | (2006.01) |
| *A61M 39/00* | (2006.01) |

(52) U.S. Cl.
CPC ..... *A61M 39/0606* (2013.01); *A61B 17/3423* (2013.01); *A61M 39/0613* (2013.01);
(Continued)

(58) Field of Classification Search
CPC ....... A61B 34/20; A61M 5/142; A61M 25/10; A61M 25/0029; A61M 2025/1063; A61M 2025/1052; A61M 2025/0031
See application file for complete search history.

(56) References Cited

U.S. PATENT DOCUMENTS

| | | | |
|---|---|---|---|
| 4,781,693 | A | 11/1988 | Martinez et al. |
| 4,960,412 | A | 10/1990 | Fink |
| (Continued) | | | |

FOREIGN PATENT DOCUMENTS

| | | |
|---|---|---|
| CN | 101563131 | 10/2009 |
| CN | 102300781 | 12/2011 |
| (Continued) | | |

OTHER PUBLICATIONS

US 5,520,663 A, 05/1996, Patterson et al. (withdrawn)
(Continued)

*Primary Examiner* — Bradley J Osinski
(74) *Attorney, Agent, or Firm* — Pauly, DeVries Smith & Deffner LLC

(57) ABSTRACT

Aspects herein relate to a low-friction septum for providing a leak-resistant seal for use in a vascular access device. In an embodiment, a device for vascular access hemostasis is included having an enclosure defining a cavity and configured to at least partially receive a medical device. The device can include a first seal portion and a second seal portion, the cavity disposed between the first seal portion and the second seal portion. The device can include a barrel in structural communication with the second seal portion, the second seal portion including a septum seal. The second seal portion can define two or more discrete portions, each separated by one or more split lines. The discrete portions can include a mating surface to interface with mating surfaces of other discrete portions. The mating surface can include a surface topology including raised portions and depressions. Other embodiments are also included herein.

18 Claims, 12 Drawing Sheets

Related U.S. Application Data

(60) Provisional application No. 62/434,785, filed on Dec. 15, 2016.

(52) U.S. Cl.
CPC ............. *A61M 2039/0072* (2013.01); *A61M 2039/062* (2013.01); *A61M 2039/064* (2013.01); *A61M 2039/066* (2013.01); *A61M 2039/068* (2013.01); *A61M 2039/0626* (2013.01); *A61M 2039/0653* (2013.01); *A61M 2205/0222* (2013.01); *A61M 2207/00* (2013.01)

(56) References Cited

U.S. PATENT DOCUMENTS

| | | |
|---|---|---|
| 4,973,493 A | 11/1990 | Guire |
| 5,092,857 A | 3/1992 | Fleischhacker et al. |
| 5,104,389 A | 4/1992 | Deem et al. |
| 5,114,408 A | 5/1992 | Fleischhaker et al. |
| 5,125,903 A | 6/1992 | Mclaughlin et al. |
| 5,195,980 A | 3/1993 | Catlin |
| 5,207,649 A | 5/1993 | Aruny |
| 5,269,764 A | 12/1993 | Vetter et al. |
| 5,300,032 A | 4/1994 | Hibbs et al. |
| 5,300,033 A | 4/1994 | Miller |
| 5,304,156 A | 4/1994 | Sylvanowicz et al. |
| 5,324,271 A | 6/1994 | Abiuso et al. |
| 5,336,192 A | 8/1994 | Palestrant |
| 5,342,315 A | 8/1994 | Rowe et al. |
| 5,414,075 A | 5/1995 | Swan et al. |
| 5,453,095 A | 9/1995 | Davila et al. |
| 5,456,284 A | 10/1995 | Ryan et al. |
| 5,507,732 A | 4/1996 | Mcclure et al. |
| 5,520,655 A | 5/1996 | Davila et al. |
| 5,549,576 A | 8/1996 | Patterson et al. |
| 5,603,702 A | 2/1997 | Smith et al. |
| 5,613,956 A | 3/1997 | Patterson et al. |
| 5,637,460 A | 6/1997 | Swan et al. |
| 5,643,227 A | 7/1997 | Stevens |
| 5,702,370 A | 12/1997 | Sylvanowicz et al. |
| 5,714,360 A | 2/1998 | Swan et al. |
| 5,748,318 A | 5/1998 | Maris et al. |
| 5,858,007 A | 1/1999 | Fagan et al. |
| 5,858,653 A | 1/1999 | Duran et al. |
| 5,935,112 A | 8/1999 | Stevens et al. |
| 6,007,833 A | 12/1999 | Chudzik et al. |
| 6,024,729 A | 2/2000 | Dehdashtian et al. |
| 6,053,861 A | 4/2000 | Grossi et al. |
| 6,077,698 A | 6/2000 | Swan et al. |
| 6,086,570 A | 7/2000 | Aboul-Hosn et al. |
| 6,142,981 A | 11/2000 | Heck et al. |
| 6,278,018 B1 | 8/2001 | Swan |
| 6,465,178 B2 | 10/2002 | Chappa et al. |
| 6,514,734 B1 | 2/2003 | Clapper et al. |
| 6,551,283 B1 | 4/2003 | Guo et al. |
| 6,569,120 B1 | 5/2003 | Cuny et al. |
| 6,603,040 B1 | 8/2003 | Swan |
| 6,632,200 B2 | 10/2003 | Guo et al. |
| 6,702,255 B2 | 3/2004 | Dehdashtian |
| 6,712,791 B2 | 3/2004 | Lui et al. |
| 6,762,019 B2 | 7/2004 | Swan et al. |
| 7,081,106 B1 | 7/2006 | Guo et al. |
| 7,101,353 B2 | 9/2006 | Lui et al. |
| 7,138,541 B2 | 11/2006 | Swan |
| 7,241,276 B2 | 7/2007 | Argentine et al. |
| 7,309,593 B2 | 12/2007 | Ofstead et al. |
| 7,348,055 B2 | 3/2008 | Chappa et al. |
| 7,582,070 B2 | 9/2009 | Goode et al. |
| 7,628,774 B2 | 12/2009 | Fangrow et al. |
| 7,731,694 B2 | 6/2010 | Becker et al. |
| 7,736,689 B2 | 6/2010 | Chappa et al. |
| 7,772,393 B2 | 8/2010 | Guire et al. |
| 7,807,750 B2 | 10/2010 | Taton et al. |
| 7,901,379 B2 | 3/2011 | Argentine et al. |
| 7,976,503 B2 | 7/2011 | Khan et al. |
| 8,016,791 B2 | 9/2011 | Sugiki et al. |
| 8,039,524 B2 | 10/2011 | Ralph et al. |
| 8,048,033 B2 | 11/2011 | Becker et al. |
| 8,096,976 B2 | 1/2012 | Sugiki et al. |
| 8,137,321 B2 | 3/2012 | Argentine et al. |
| 8,172,806 B2 | 5/2012 | Smith |
| 8,177,760 B2 | 5/2012 | Rome et al. |
| 8,246,585 B2 | 8/2012 | Schennib et al. |
| 8,273,059 B2 | 9/2012 | Nardeo et al. |
| 8,444,628 B2 | 5/2013 | Fangrow et al. |
| 8,487,137 B2 | 7/2013 | Guire et al. |
| 8,513,320 B2 | 8/2013 | Rooijmans |
| 8,523,822 B2 | 9/2013 | Nardeo et al. |
| 8,779,206 B2 | 7/2014 | Guire et al. |
| 8,790,309 B2 | 7/2014 | Goode et al. |
| 8,809,411 B2 | 8/2014 | Rooijmans |
| 8,870,850 B2 | 10/2014 | Fangrow et al. |
| 8,889,760 B2 | 11/2014 | Kurdyumov et al. |
| 8,932,694 B2 | 1/2015 | Rolfes Meyering |
| 9,005,172 B2 | 4/2015 | Chung |
| 9,108,032 B2 | 8/2015 | Melsheimer |
| 9,410,044 B2 | 8/2016 | Kurdyumov |
| 9,522,266 B2 | 12/2016 | Sutton et al. |
| 10,391,292 B2 | 8/2019 | Sutton |
| 10,758,719 B2 | 9/2020 | Olson |
| 2003/0050604 A1 | 3/2003 | Lui et al. |
| 2004/0082923 A1 | 4/2004 | Field |
| 2004/0210194 A1 | 10/2004 | Bonnette et al. |
| 2004/0260243 A1 | 12/2004 | Rickerd |
| 2005/0020981 A1 | 1/2005 | Kurth et al. |
| 2007/0032882 A1 | 2/2007 | Lodhi et al. |
| 2009/0012476 A1 | 1/2009 | Catlin |
| 2009/0125103 A1 | 5/2009 | Molgaard-nielsen |
| 2009/0209914 A1 | 8/2009 | Koch et al. |
| 2009/0259175 A1 | 10/2009 | Nordgren |
| 2010/0030164 A1 | 2/2010 | Kimball et al. |
| 2010/0198168 A1 | 8/2010 | Rooijmans |
| 2010/0241078 A1 | 9/2010 | Barnes |
| 2010/0292638 A1 | 11/2010 | Becker et al. |
| 2010/0331784 A1 | 12/2010 | Fisher et al. |
| 2011/0040260 A1 | 2/2011 | Leeflang et al. |
| 2011/0144373 A1 | 6/2011 | Swan et al. |
| 2012/0083750 A1 | 4/2012 | Sansoucy |
| 2012/0148852 A1 | 6/2012 | Jelle et al. |
| 2012/0149934 A1 | 6/2012 | Kurdyumov |
| 2012/0221024 A1 | 8/2012 | Sutton et al. |
| 2012/0245527 A1 | 9/2012 | Stephens et al. |
| 2012/0296274 A1 | 11/2012 | Slager |
| 2013/0143056 A1 | 6/2013 | Swan et al. |
| 2014/0343512 A1 | 11/2014 | Fischer et al. |
| 2015/0140107 A1 | 5/2015 | Slager et al. |
| 2015/0157843 A1 | 6/2015 | Pepin et al. |
| 2016/0081715 A1 | 3/2016 | Kleyman |
| 2016/0175489 A1 | 6/2016 | Babcock et al. |
| 2017/0361083 A1 | 12/2017 | Sutton |
| 2018/0169396 A1 | 6/2018 | Olson |
| 2020/0086106 A1 | 3/2020 | Sutton |

FOREIGN PATENT DOCUMENTS

| | | |
|---|---|---|
| CN | 102573676 | 7/2012 |
| CN | 103260695 | 8/2013 |
| CN | 203556057 | 4/2014 |
| CN | 109310856 | 2/2019 |
| CN | 110167626 | 8/2019 |
| EP | 0143518 | 6/1985 |
| EP | 2351533 | 8/2011 |
| EP | 3471818 | 4/2019 |
| EP | 3554623 | 10/2019 |
| EP | 3554623 | 8/2022 |
| EP | 4082598 | 11/2022 |
| JP | S6077766 | 5/1985 |
| JP | 2011502023 | 1/2011 |
| JP | 2020501705 | 1/2020 |
| KR | 20030060424 | 7/2003 |
| WO | 0012171 | 3/2000 |
| WO | 2007044879 | 4/2007 |
| WO | 2010087943 | 8/2010 |

(56) References Cited

FOREIGN PATENT DOCUMENTS

| WO | 2010087943 | 7/2011 |
| WO | 2012118852 | 9/2012 |
| WO | 2017218634 | 12/2017 |
| WO | 2018112031 | 6/2018 |

OTHER PUBLICATIONS

"Communication Pursuant to Article 94(3) EPC," for European Patent Application No. 17732694.9 dated Oct. 8, 2019 (5 pages).
File History for U.S. Appl. No. 15/838,677 downloaded Nov. 14, 2020 (261 pages).
"First Office Action," for Chinese Patent Application No. 201780034900X dated Sep. 21, 2020 (18 pages) with English Translation.
"International Preliminary Report on Patentability," for PCT Application No. PCT/US2017/037410 dated Dec. 27, 2018 (8 pages).
"International Preliminary Report on Patentability," for PCT Application No. PCT/US2017/066091 dated Jun. 27, 2019 (10 pages).
"International Preliminary Report on Patentability," for PCT/US2012/027012, dated Sep. 12, 2013 (5 pages).
"International Search Report and Written Opinion," for PCT Application No. PCT/US2012/027012, dated Sep. 28, 2012 (9 pages).
"International Search Report and Written Opinion," for PCT Application No. PCT/US2017/037410 dated Sep. 25, 2017 (11 pages).
"International Search Report and Written Opinion," for PCT Application No. PCT/US2017/066091 dated Mar. 20, 2018 (14 pages).
"Non-Final Office Action," for U.S. Appl. No. 15/620,008 dated Oct. 31, 2018 (24 pages).
"Notice of Allowance," for U.S. Appl. No. 15/620,008 dated Apr. 16, 2019 (8 pages).
"Response to Communication Pursuant to Article 94(3) EPC," for European Patent Application No. 17732694.9 filed Feb. 14, 2020 (12 pages).
"Response to Communication Pursuant to Rules 161(1) and 162 EPC," for European Patent Application No. 17732694.9 filed Jul. 31, 2019 (17 pages).
"Response to Communication Pursuant to Rules 161(1) and 162 EPC," for European Patent Application No. 17822977.9 filed Feb. 3, 2020 (13 pages).
"Response to Non-Final Rejection," dated Oct. 31, 2018, for U.S. Appl. No. 15/620,008 submitted via EFS-Web on Jan. 29, 2019, 8 pages.
"First Office Action," for Chinese Patent Application No. 201780081806 dated Jan. 22, 2021 (21 pages) with English Translation.
"Office Action," for Japanese Patent Application No. 2019-531918 dated Aug. 16, 2021 (5 pages) with English Translation.
"Second Office Action," for Chinese Patent Application No. 201780034900 dated Mar. 23, 2021 (16 pages) with English translation.
"Second Office Action," for Chinese Patent Application No. 201780081806 dated Sep. 3, 2021 (13 pages) with English translation.
"Communication Pursuant to Article 94(3) EPC," for European Patent Application No. 17732694.9 dated Oct. 25, 2022 (4 pages).
"Extended European Search Report," for European Patent Application No. 22180549.2 dated Jul. 27, 2022 (8 pages).
"Non-Final Office Action," for U.S. Appl. No. 16/549,564 dated Aug. 30, 2022 (28 pages).
"Office Action," for Japanese Patent Application No. 2018-531918 dated Nov. 5, 2021 (3 pages) with English translation.
"Office Action," for Mexican Patent Application No. MX/a/2018/015569 dated Sep. 5, 2022 (4 pages) with English Summary.
"Response to Non-Final Office Action," for U.S. Appl. No. 16/549,564, filed Nov. 29, 2022 (10 pages).
"Non-Final Office Action," for U.S. Appl. No. 16/549,564 dated Jun. 16, 2023 (17 pages).
"Response to Communication Pursuant to Article 94(3) EPC," for European Patent Application No. 17732694.9 filed Mar. 21, 2023 (10 pages).
"Response to Communication Pursuant to Rule 69 EPC," for European Patent Application No. 22180549.2 filed Apr. 28, 2023 (21 pages).
"Response to Final Office Action," for U.S. Appl. No. 16/549,564 filed May 23, 2023 (10 page).

LOW-FRICTION SEALING DEVICES

This application is a continuation application of U.S. patent application Ser. No. 15/838,677, filed Dec. 12, 2017, now U.S. Pat. No. 10,758,719, issued Sep. 1, 2020, which claims the benefit of U.S. Provisional Application No. 62/434,785, filed Dec. 15, 2016, the contents of which are herein incorporated by reference.

FIELD

Aspects herein relate to a low-friction sealing device for providing a leak-resistant seal for use in a vascular access device.

BACKGROUND

When interventional catheter devices are inserted into the vascular system, the physician usually starts with a needle stick, followed by dilating the artery in order to insert an introducer sheath device that is left in place for the duration of the procedure. This introducer sheath acts as the main conduit for entry of subsequent therapeutic or diagnostic devices.

In most instances, these introducer sheaths contain a hemostatic component that restricts back-flow of blood from the artery. These hemostasis seals are generally passive and provide sealing around the catheter devices and guide wires that are used during the procedure. In some cases, hemostasis seals can include a septum structure or seal, though which a device such as a guide wire or other medical device component is inserted in order to pass through the hemostasis seal.

SUMMARY

Aspects herein relate to a low-friction sealing devices for providing a leak-resistant seal for use in a vascular access device. In an embodiment a device for vascular access hemostasis is included. The device can include an enclosure configured to at least partially receive a medical device, the enclosure defining a cavity. The device can include a first seal portion and a second seal portion. The cavity can be disposed between the first seal portion and the second seal portion. The device can include a barrel in structural communication with the second seal portion. The second seal portion can include a septum seal. The second seal portion can define two or more discrete portions, each separated from one another by one or more split lines. The discrete portions can each include a mating surface configured to interface with mating surfaces of other discrete portions. The mating surface can include a surface topology including a plurality of raised portions and depressions.

In an embodiment a sealing device is included. The sealing device can include a device enclosure defining a cavity. The device enclosure can be configured to compressively interface with a housing. The sealing device can include a first seal portion in communication with the device enclosure, the first seal portion defining an opening. The sealing device can include a second seal portion in communication with the device enclosure. The second seal portion can define two or more discrete portions separated from one another by a split along a split plane. The discrete portions can each include a mating surface to interface with mating surfaces of other discrete portions, the mating surface having a surface topology including a plurality of raised portions and depressions.

In an embodiment a method of making a sealing device is included. The method can include obtaining an enclosure configured to at least partially receive a medical device, the enclosure defining a cavity and having a first seal portion and a second septum seal portion. The cavity can be disposed between the first seal portion and the second septum seal portion. The method can further include forming a split in the second seal portion, the split defining discrete portions each comprising a mating surface to interface with mating surfaces of other discrete portions. The mating surface can include a surface topology including a plurality of raised portions and depressions.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

Aspects herein can be more completely understood in consideration of the following detailed description of various embodiments in connection with the accompanying drawings, in which.

These drawings are to be considered general representations of some embodiments, and it will be appreciated that they are not drawn to encompass all embodiments, nor are they always drawn to scale. While aspects herein are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope of that described herein.

DETAILED DESCRIPTION

Hemostasis valves need to provide for the passage of vascular access components and medical devices while also providing a sealing function. The insertion of vascular access components and/or medical devices (inserted components) into a hemostasis valve can be hindered by friction between the inserted components and surfaces within the hemostasis valve that the inserted components contact as they inserted. Excess friction can undesirably increase the amount of force required to insert components into the hemostasis valve.

Embodiments herein provide for low-friction hemostasis seal structures and low-friction portions thereof, such as low-friction septums, to reduce the amount of force required to insert a vascular access component and or medical device into a hemostasis seal structure.

In some embodiments, devices herein can include a hydrophilic coating providing lubricious properties to a first seal portion and/or areas of the device adjacent to the first seal portion in order to reduce the friction and insertion force required to insert a device through the first seal portion. In various embodiments, hydrophilic coatings can also be disposed over other portions of the hemostasis sealing device.

In some embodiments, devices herein can include a surface topology with raised portions and depressions reducing the contact area between a second seal portion and a device passing there through, thereby reducing the friction and insertion force required to insert a device through the second seal portion.

In some embodiments, the first seal portion can be a hole seal or a ring seal, while the second seal portion can be a split, septum seal. The hemostasis sealing device can include structural elements that are configured to structurally support the second seal portion for sealing. In a variety of embodiments, the second seal portion is held in compression by a housing that compressively interfaces with the hemostasis sealing device. In such an embodiment, support ribs can be in compressive communication with the second seal portion. The split of the second seal portion can be an axial split offset from the support ribs. In some implementations a barrel extends from the second seal portion to inhibit seal inversion or misalignment.

Figure 1:
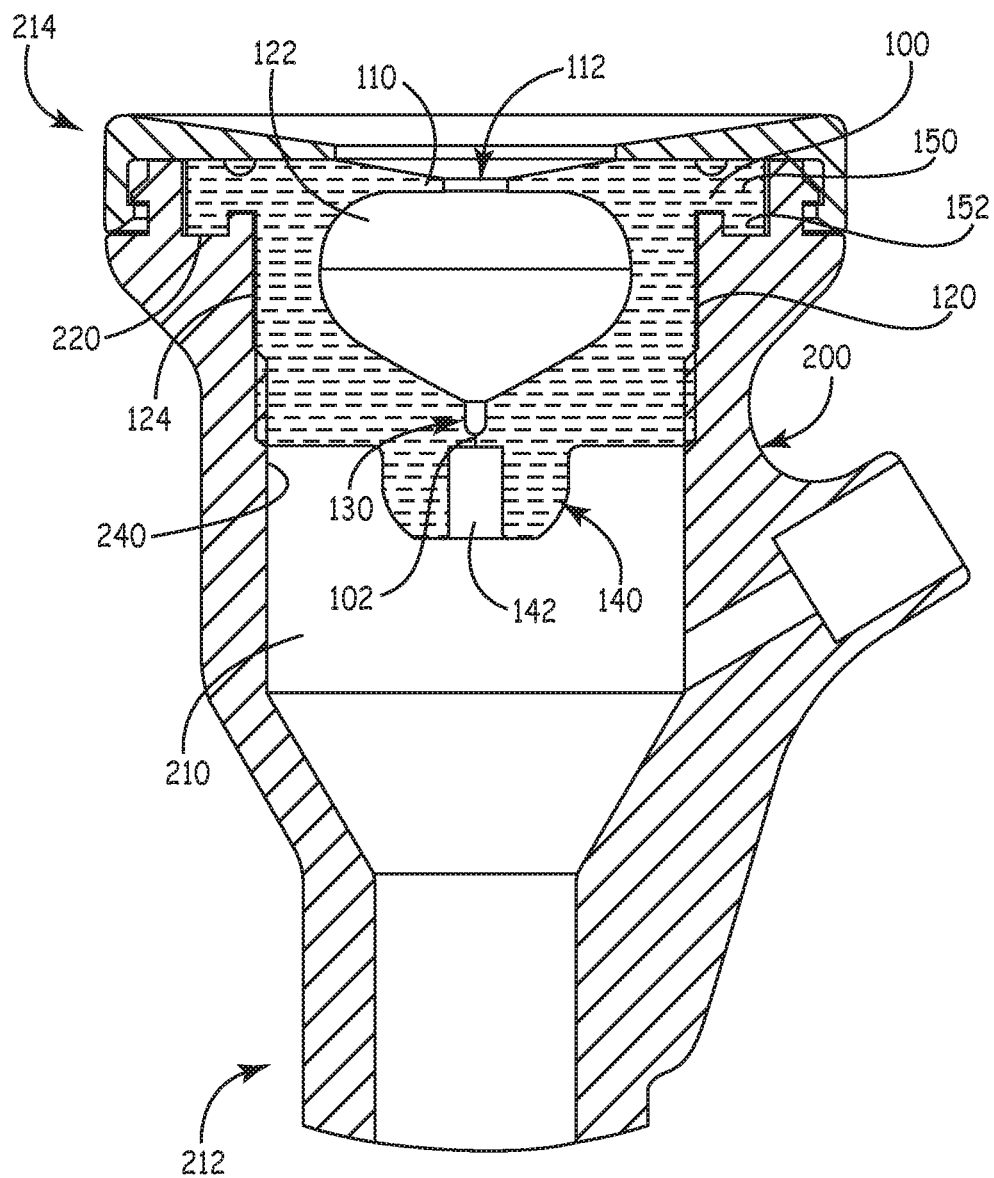
FIG. 1 is a cross-sectional view of an example hemostasis sealing device consistent with the technology disclosed herein.

An example embodiment of such a hemostasis sealing device is shown in FIG. 1. The hemostasis sealing device 100 is disposed in a housing 200 and has a device enclosure 120 in communication with a first seal portion 110 on a support ring 150, a second seal portion 130, and a barrel 140. The housing 200 can be an introducer sheath, but could be another device that is generally rigid and defines a passageway 210 extending from the proximal end 214 of the housing 200 to a distal end 212 of the housing 200.

The hemostasis sealing device 100 can be configured to provide a fluid seal for vascular access devices and simultaneously allowing translation or movement of a guide wire while providing a fluid seal there-around. The hemostasis sealing device 100 can be constructed of a variety of materials such as, for example, silicone rubber in the range of 10-60 Shore A durometer. In another example, the hemostasis sealing device 100 can be constructed so as to contain nitinol elements. Those having skill in the art will recognize that the hemostasis sealing device 100 can be constructed of various thermoplastic elastomers, and combinations thereof, available and known.

The hemostasis sealing device 100 is configured to be received by the proximal end 214 of the housing 200. In at least one embodiment the hemostasis sealing device 100 is in compression upon being received by the housing 200. In one embodiment the compression of the hemostasis sealing device 100 is in the range of 0-5% of the diameter of the seal body. This compression allows the hemostasis sealing device 100 to be firmly held within the housing 200.

The hemostasis sealing device 100 has a device enclosure 120 defining a device cavity 122 and, as mentioned above, has the first seal portion 110 and the second seal portion 130. The first seal portion 110 can be configured to provide a seal for a medical device passing into the device cavity 122, such as a vascular access device, and the second seal portion 130 can be configured to provide a seal for a guide wire. The device cavity 122 can be sized to receive at least a portion of the medical device.

In this particular embodiment, the support ring 150 has a radial flange 152 and is received by a ring receptacle 220 defined by the housing 200. In some embodiments, the support ring 150 will be relatively rigid compared to some portions of the hemostasis sealing device 100. An outer annular surface 124 of the hemostasis sealing device 100 is received by the proximal end 214 of the passageway 210 of the housing 200. In at least one embodiment, the housing 200 exerts compressive force on the outer annular surface 124 of the hemostasis sealing device 100.

The first seal portion 110 can be elastomeric and defines a first seal opening 112 that is sized to seal around the medical device passing there-through. In one embodiment, the first seal portion 110 is a sealing hole. In another embodiment, the first seal portion 110 is a sealing ring. Typically the first seal opening 112 defined by the first seal portion 110 is sized in the range of 0.2-0.4 times the diameter of the largest device size that is to be inserted through a given seal. For instance, for a 20 Fr device (0.260 in. diameter), the first seal opening 112 size would be in the range of 0.052-0.104 in. in diameter.

The second seal portion 130 is similarly elastomeric to the first seal portion 110 and defines a split 102 there-through. The split 102 can be axial relative to the second seal portion 130, and can also be axial relative to the hemostasis sealing device 100 itself. In a variety of embodiments, the second seal portion 130 has a thickness in the range of 0.005-0.020 inches and a diameter in the range of 0.9-1.3 times the diameter of the guide wire to be used. Given the size differential between the first seal portion 110 and the second seal portion 130, in the current embodiment, the cross section of the device cavity 122 generally tapers towards the second seal portion 130. Those having skill in the art will recognize that the second seal portion 130 can be consistent with a split septum seal. In a variety of embodiments, structural elements of the hemostasis sealing device 100 are configured to provide structural support to the second seal portion 130. As one example, the compression fit between the hemostasis sealing device 100 and the housing 200 compresses the second seal portion 130 at the split 102 to be in sealing engagement with a guide wire.

A barrel 140 of the hemostasis sealing device 100 can extend from the second seal portion 130. The barrel 140 can be annular and coaxial with the second seal portion 130. The barrel 140 defines a barrel opening 142, a substantial portion of which is cylindrical in shape. The barrel 140 can be configured to provide structural support to the second seal portion 130. In at least one embodiment, the barrel 140 prevents the split 102 of the second seal portion 130 from becoming misaligned and/or inverted on itself, wherein misalignment and inversion can inhibit complete sealing.

Figure 2:
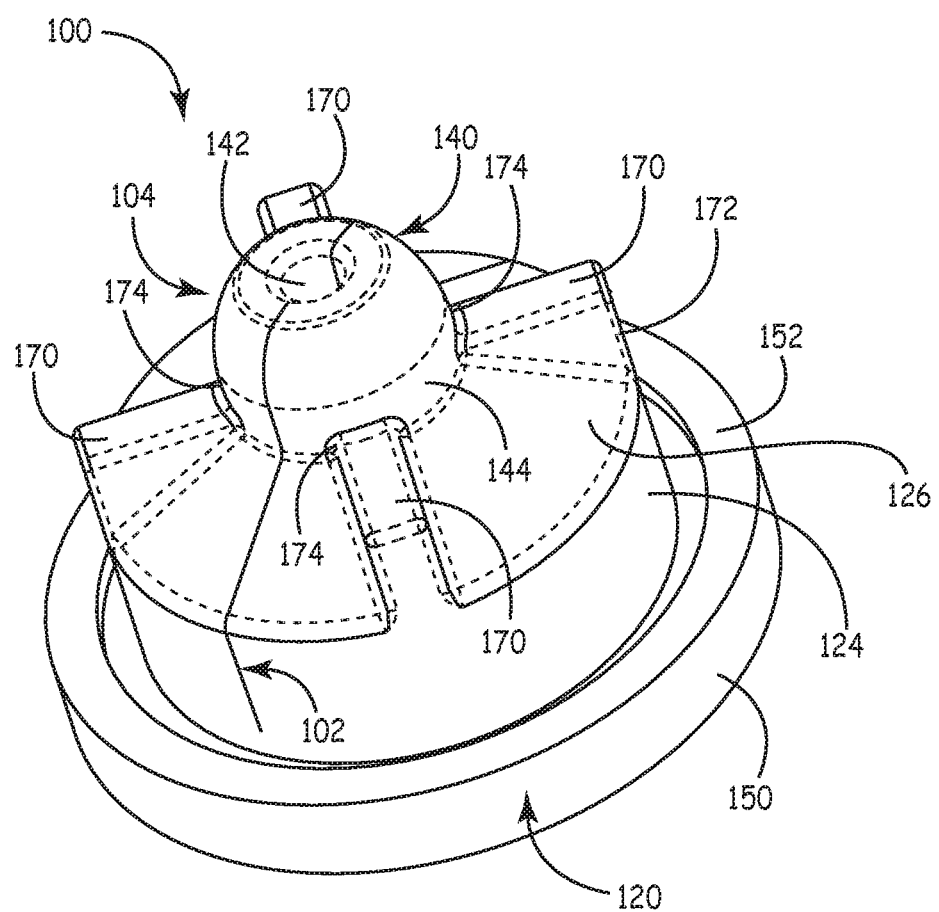
FIG. 2 is a perspective view of an example hemostasis sealing device consistent with the technology disclosed herein.

FIG. 2 depicts a perspective view of the hemostasis sealing device 100 of FIG. 1. From this view the overall configuration of the split is more clearly visible and the outer configuration of the device enclosure 120 and the support ribs 170 are visible.

The split 102 can be defined from the proximal end 104 of the hemostasis sealing device 100, through the barrel 140 and the device enclosure 120, and extending towards the support ring 150. In a variety of embodiments the split 102 does not extend through the support ring 150 or the first seal portion 110. In a variety of implementations, it can be desirable for the hemostasis sealing device 100 to allow passage of large-bore devices, and the split 102 defined by the hemostasis sealing device 100 can accommodate such a use.

A tapered portion 126 of the device enclosure 120 extends between the outer annular surface 124 of the device enclosure 120 and the barrel 140. The tapered portion 126 can correspond with the tapered shape of the device cavity 122 and can extend adjacent to the second seal portion 130 (See FIG. 1). In the current embodiment the tapered portion 126, the annular surface 124, and the barrel 140 are a single cohesive unit. In some embodiments the annular surface 124, the barrel 140, and the tapered portion 126 can be an assembly of multiple components.

In a variety of implementations the hemostasis sealing device 100 includes two or more support ribs 170 along the tapered portion 126 of the device enclosure 120 in compressive communication with at least a portion of the split 102. As depicted in FIG. 2, the current embodiment has four support ribs 170. The support ribs 170 can be configured to provide structural support to the hemostasis sealing device 100 when the hemostasis sealing device 100 is installed in a housing, such as the housing depicted in FIG. 1. The support ribs 170 can provide structural support to the hemostasis sealing device 100 particularly along the split 102 to ensure sealing of the second seal portion 130 (visible in FIG. 1) despite insertion of a medical device in the device enclosure 120.

In the current embodiment, an outer end surface 172 of each support rib 170 is coplanar with the outer annular surface 124 of the device enclosure 120. As such, the outer annular surface 124 of the device enclosure 120, the outer end surface 172 of each support rib 170 is configured for compressive interfacing with the inner annular surface 240 of the housing 200 (See FIG. 1). An inner end 174 of each support rib 170 contacts the outer surface 144 of the barrel 140, which can be adjacent to the second seal portion 130 (See FIG. 1). As such, despite expansion forces from the device cavity 122 and the first seal opening 112 (See FIG. 1) on the hemostasis sealing device 100 upon medical device insertion, reactive compressive forces by the housing 200 are exerted, in part, on the support ribs 170 and transferred to the barrel 140 and, therefore, around the second seal portion 130 of the hemostasis sealing device 100. Such compressive forces can prevent separation of the hemostasis sealing device 100 at least around the second seal portion 130.

It can be desirable to stagger the split 102 defined by the hemostasis sealing device 100 relative to the support ribs 170 such that relatively symmetrical compressive forces are applied about the second seal portion 130. In the current embodiment, the support ribs 170 are symmetrical relative to the split 102. The split 102 is offset from the support ribs 170 by about 45 degrees. Other configurations of support ribs relative to a split defined by a hemostasis sealing device are also possible.

Figure 3:
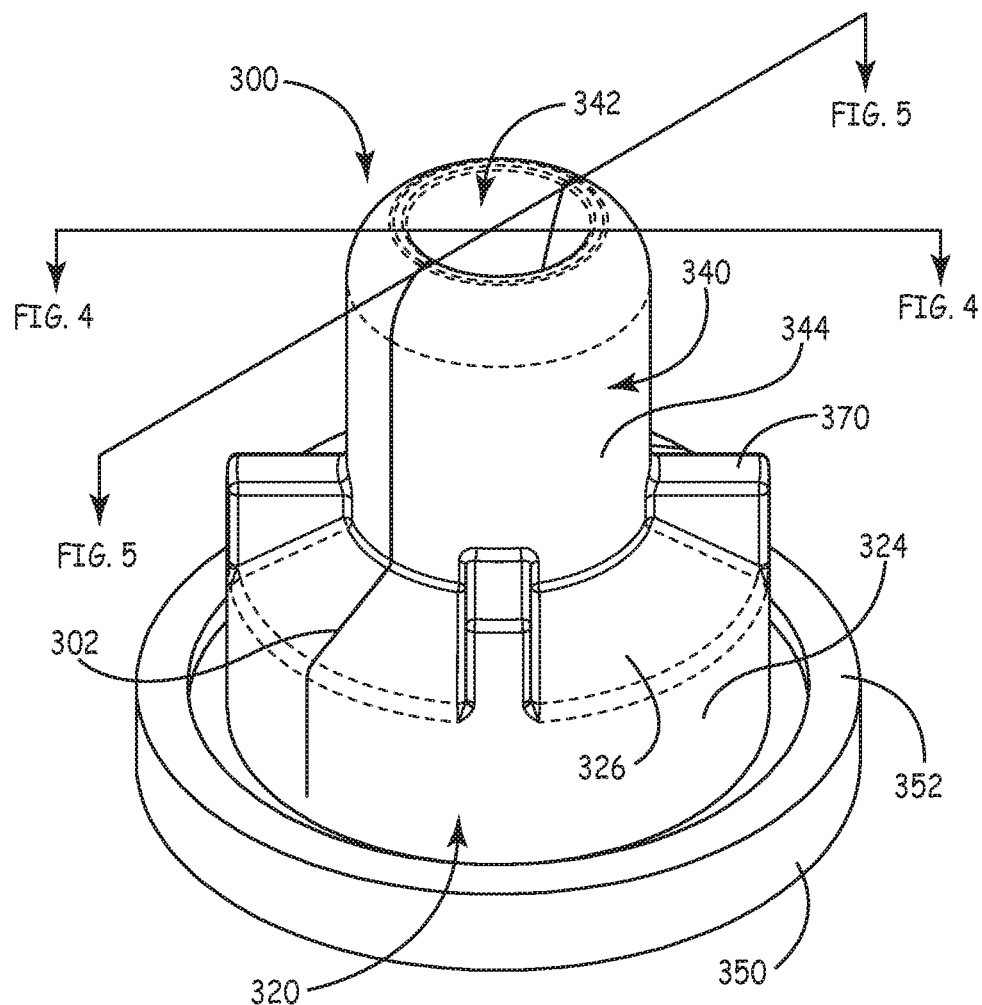
FIG. 3 is a perspective view of another example hemostasis sealing device consistent with the technology disclosed herein.

FIG. 3 is a perspective view of another embodiment of a hemostasis sealing device consistent with the technology disclosed herein. Similar to the hemostasis sealing device 100 depicted in FIG. 2, this hemostasis sealing device 300 has a device enclosure 320 with a first sealing portion and a second sealing portion (not visible in this view). The hemostasis sealing device 100 has a support ring 350 having a flange 352 coupled to the device enclosure 320 that has an outer annular surface 324 and a tapered portion 326. A barrel 340 defining an opening 342 is coupled to the tapered portion 326 and support ribs 370 extend along the tapered portion 326 from the outer annular surface 324 of the device enclosure 320 to the outer surface 344 of the barrel 340. A split 302 is defined by the hemostasis sealing device 300 from the proximal end 304 of the hemostasis sealing device 300 towards the support ring 350. The split 302 can extend through the barrel 340 and the device enclosure 320. However, it will be appreciated that in various embodiments the split is not as broad as shown in FIG. 3 and does not extend through the width of the barrel 340.

Figure 5:
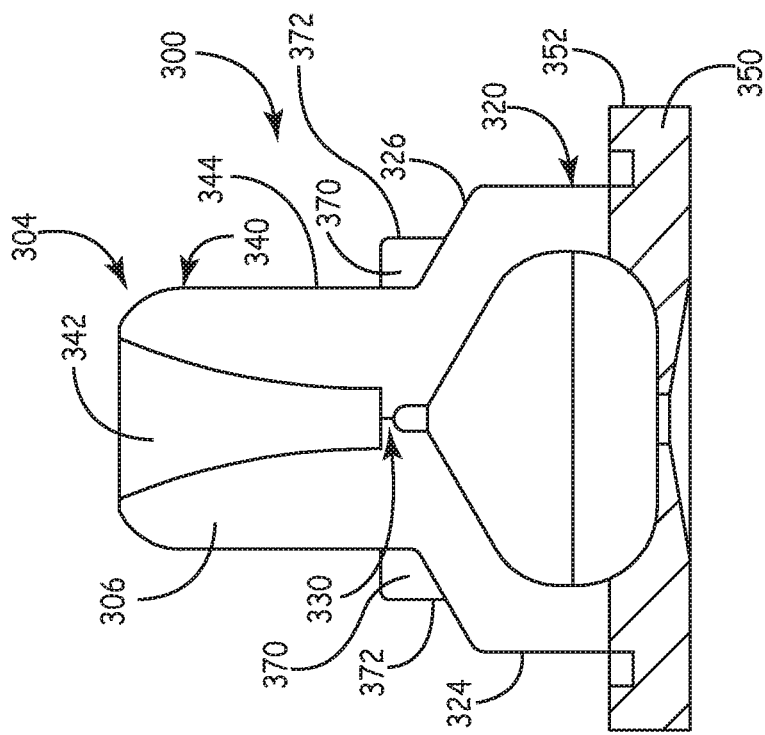
FIG. 5 is another cross-sectional view of the hemostasis sealing device of FIG. 3.
Figure 4:
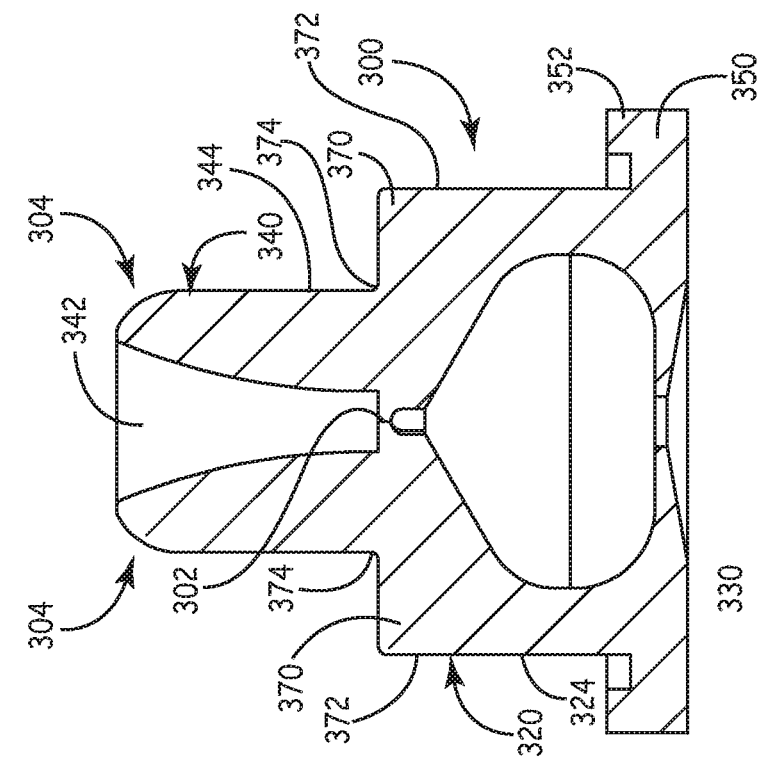
FIG. 4 is a cross-sectional view of the hemostasis sealing device of FIG. 3.

FIGS. 4 and 5 are cross-sectional views consistent with the hemostasis sealing device 300 of FIG. 3, as notated on FIG. 3. Specifically, FIG. 4 is a cross-sectional view of the hemostasis sealing device 300 through opposing support ribs 370. FIG. 5 is a cross-sectional view of the hemostasis sealing device 300 along the split 302 (See FIG. 3) revealing a split-defining surface 306 of the hemostasis sealing device 300 that is adjacent to the split 302 (FIG. 3). In FIG. 5 it is visible that the split-defining surface 306 and, therefore, the split 302 itself, extends from the proximal end 304 of the hemostasis sealing device 300, through the barrel 340 and the device enclosure 320 to the support ring 350. In the current embodiment the support ring 350 does not define any portion of the split 302.

Visible in FIG. 5, the annular surface 324 of the device enclosure 320 has a tapered portion 326 that couples to the barrel 340. Similar to the embodiment depicted in FIGS. 1-2, the support ribs 370 of the hemostasis sealing device 300 of FIGS. 3-5 are disposed along the tapered portion 326 and each have an outer end surface 372 that is substantially coplanar with the outer annular surface 324 of the device enclosure 320 and an inner end 374 adjacent to the second sealing portion 330. The inner end 374 of each rib 370 generally meets the outer surface 344 of the barrel 340. There are four support ribs 370 in this particular embodiment, which are staggered 45 degrees from the split 302.

In the embodiment depicted in FIGS. 4 and 5, the barrel opening 342 defined by the barrel 340 is at least partially tapered from the second seal portion 330 to the proximal end 304 of the hemostasis sealing device 300. Such a configuration can help prevent inversion of the second seal portion 330. Those having skill in the art will appreciate other configurations that could have similar advantages regarding the second seal portion 330.

Figure 6:
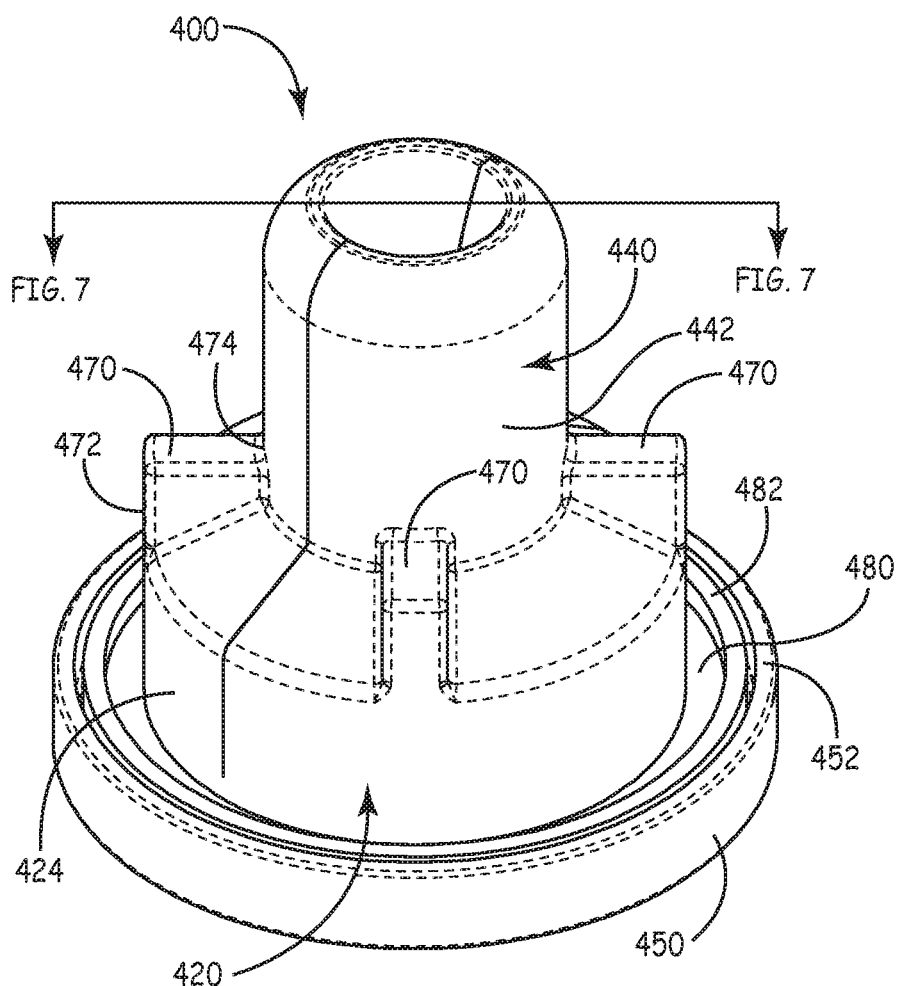
FIG. 6 is a perspective view of another example hemostasis sealing device consistent with the technology disclosed herein.
Figure 7:
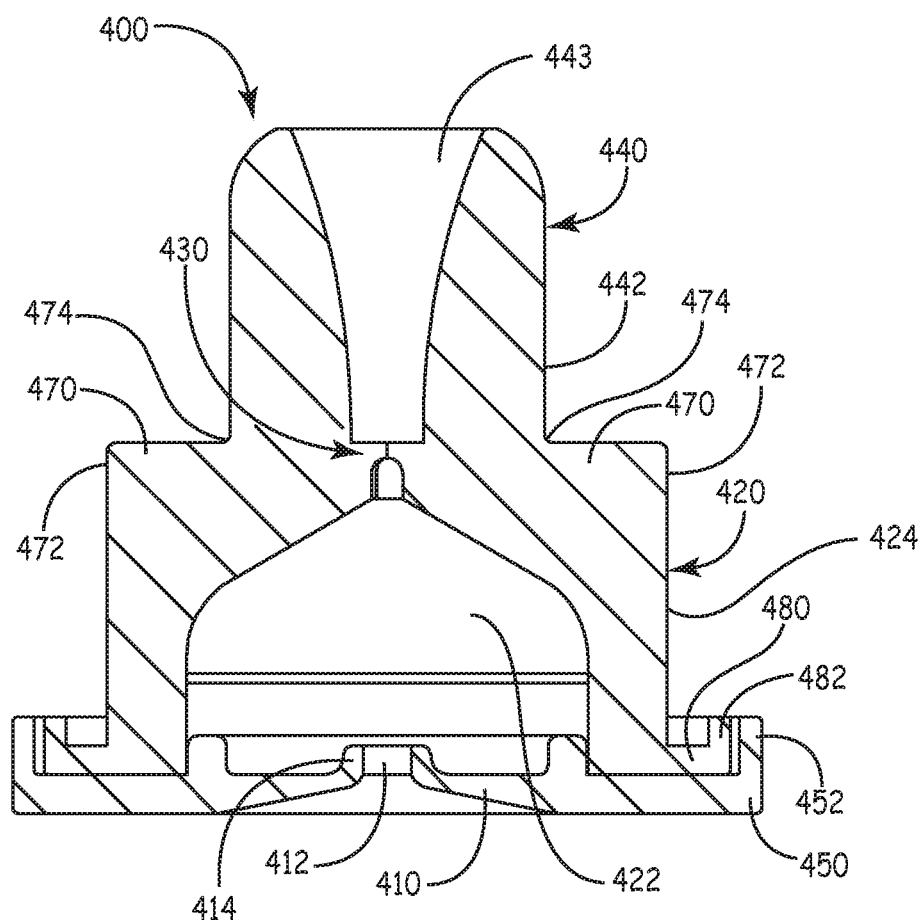
FIG. 7 is a cross-sectional view of the hemostasis sealing device of FIG. 6.

FIG. 6 is a perspective view of another embodiment of a hemostasis sealing device consistent with the technology disclosed herein. FIG. 7 is a cross-sectional view of the hemostasis sealing device 400 of FIG. 6. In this embodiment a first seal portion 410 and the second seal portion 430 are manufactured as separate components and are coupled to form a cohesive unit. The first seal portion 410 is defined by a support ring 450 having a flange 452 that is configured to engage a device enclosure 420 defining the second seal portion 430. A barrel 440 extends from the device enclosure 420 and is configured to provide structural support to the second seal portion 430. Support ribs 470 are additionally configured to provide structural support to the second seal portion 430. Each support rib 470 has an outer end surface 472 that is substantially coplanar with the outer annular surface 424 of the device enclosure 420 and an inner end 474 in compressive communication with the second seal portion 430. Each support rib 470 is configured to exert compressive force on the second seal portion 430, through the barrel outer surface 442, upon insertion of the hemostasis sealing device 400 in a housing such as an introducer sheath.

In the current embodiment the first seal portion 410 has a radial lip 414 extending into the device cavity 422 that at least partially defines a first seal opening 412. The radial lip 414 can be configured to contribute to device sealing around a medical device.

The support ring 450 can be coupled to the device enclosure 420 through a variety of ways that will be known in the art. In one embodiment an adhesive is disposed between the support ring 450 and the device enclosure 420 to couple the components. In another embodiment the support ring flange 452 threadably engages a mating structure 480 defined by the device enclosure 420. The mating structure 480 can include a mating flange 482 that is configured to be concentric to the flange 452 of the support ring 450. The mating flange 482 can define a threaded surface that is configured to be received by the support ring flange 452. In some embodiments the support ring 450 is configured to be permanently fixed to the device enclosure 460. In other embodiments the support ring 450 is configured to be removably fixed to the device enclosure 460. Other configurations will be appreciated by those having skill in the art.

Figure 8:
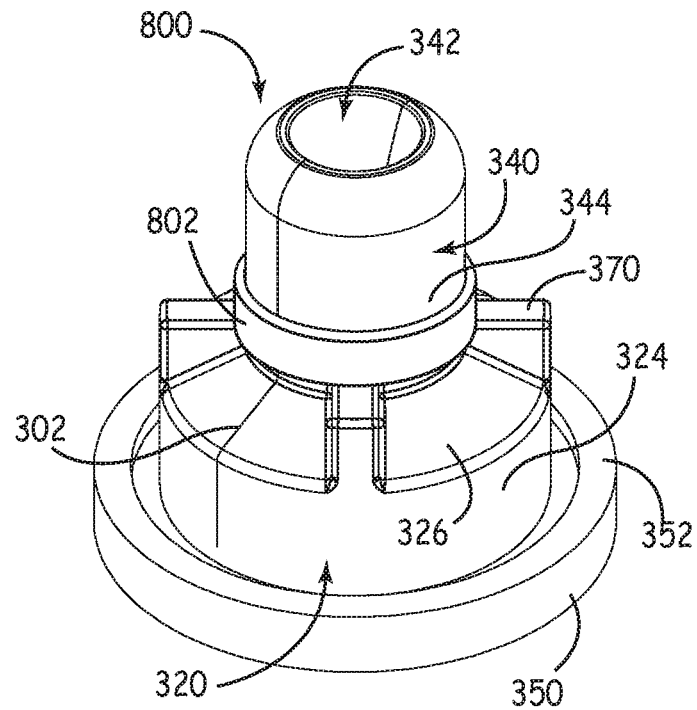
FIG. 8 is a perspective view of a hemostasis sealing device in accordance with various other embodiments.

Referring now to FIG. 8, a perspective view is shown of a hemostasis sealing device in accordance with various other embodiments. The hemostasis sealing device 800 has a device enclosure 320 with a first sealing portion and a second sealing portion (not visible in this view). The hemostasis sealing device 800 has a support ring 350 having a flange 352 coupled to the device enclosure 320 that has an outer annular surface 324 and a tapered portion 326. A barrel 340 defining an opening 342 is coupled to the tapered portion 326 and support ribs 370 extend along the tapered portion 326 from the outer annular surface 324 of the device enclosure 320 to the outer surface 344 of the barrel 340. A split 302 is defined by the hemostasis sealing device 300 from the proximal end 304 of the hemostasis sealing device 300 towards the support ring 350. The split 302 can extend through the barrel 340 and the device enclosure 320. However, it will be appreciated that in some embodiments the split 302 is not nearly as broad as that shown in FIG. 8.

The hemostasis sealing device includes a constriction ring 802 that is disposed around the barrel 340. In some embodiments, the constriction ring 802 is disposed around the barrel 340 between the support ribs 370 and the proximal end 304.

The constriction ring 802 can interface with the second seal portion to limit movement of the split, septum seal. The constriction ring 802 can be formed of various materials. In some embodiments, the constriction ring 802 includes an elastomeric material, such as an elastomeric polymer. In some embodiments, the constriction ring 802 can be formed of the same material as the barrel 340. In other embodiments, the constriction ring 802 and the barrel 340 are formed of two different materials. In some embodiments, the constriction ring 802 can be sized with an inner diameter (while unstretched) that is approximately equal to the outer diameter of the portion of the barrel 340 that it directly contacts. In other embodiments, the constriction ring 802 can be sized with an inner diameter (while unstretched) that is slightly smaller than the outer diameter of the portion of the barrel 340 that it directly contacts, such that it exerts a compressive force on the barrel 340 continuously.

In some embodiments, the barrel 340 does not include surface features to aid in retaining the constriction ring 802. However, in other embodiments, the surface of the barrel 340 can define a channel or notch into which the constriction ring 802 fits. In some embodiments, the barrel 340 can include a retaining flange on the surface thereof in order to help retain the constriction ring 802 in position Referring now to FIG. 9, a cross-sectional view is shown of the hemostasis sealing device 800 of FIG. 8. In this view, it can be seen that the barrel 340 defines a notch (or channel) 904, into which the constriction ring 802 fits. The notch 904 can be disposed around the outer perimeter of the barrel and can be configured to receive the constriction ring 802. Referring to now to FIG. 10, a cross-sectional view is shown of the hemostasis sealing device 800 of FIG. 8. A retaining flange 1008 is disposed on the surface of the barrel 340. In some cases, the barrel itself can define a retaining flange around the outer perimeter of the barrel. The retaining flange 1008 can be disposed between the constriction ring 802 and the proximal end 304.

It will be appreciated that in some embodiments, the hemostasis sealing device 800 can include both a notch and a retaining flange.

Figure 9:
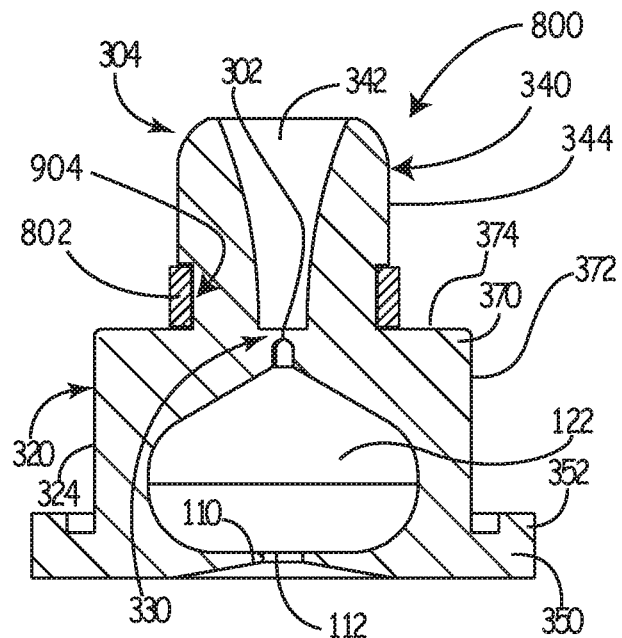
FIG. 9 is a cross-sectional view of the hemostasis sealing device of FIG. 8.
Figure 10:
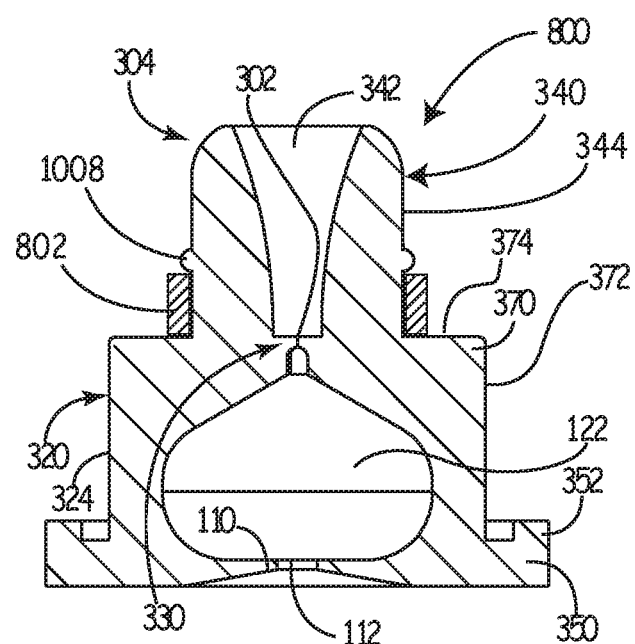
FIG. 10 is a cross-sectional view of a hemostasis sealing device in accordance with various embodiments.

Although the constriction ring 802 as shown in FIGS. 8-10 is substantially polygonal in cross-section (and rectangular in particular), the constriction ring 802 can take on many different shapes in cross-section. For example, the constriction ring 802 can also be square, non-polygonal (such as circular or oval), irregular, or the like.

In some embodiments, a method of making a sealing device is included. The method can include obtaining an enclosure configured to at least partially receive a medical device. The enclosure can define a cavity and can have a first seal portion and a second seal portion, the cavity disposed between the first seal portion and the second seal portion. The second seal portion can include a split, septum seal. The method can further include disposing a constriction ring around the enclosure, the constriction ring interfacing with the split, septum seal to limit movement of the split, septum seal.

In some embodiments, one or more surfaces of the hemostasis sealing device can include a surface topology with raised portions and depressions so that a reduced surface area is presented to anything that contacts that portion of the hemostasis sealing device. Reducing the surface area can reduce the friction of anything contacting the surface. For example, mating surfaces associated with the second seal portion can be modified to have a surface topology that minimizes the surface area contacting any device passing through the second seal portion. In this way the amount of force required to push a device through the second seal portion can be reduced.

Figure 11:
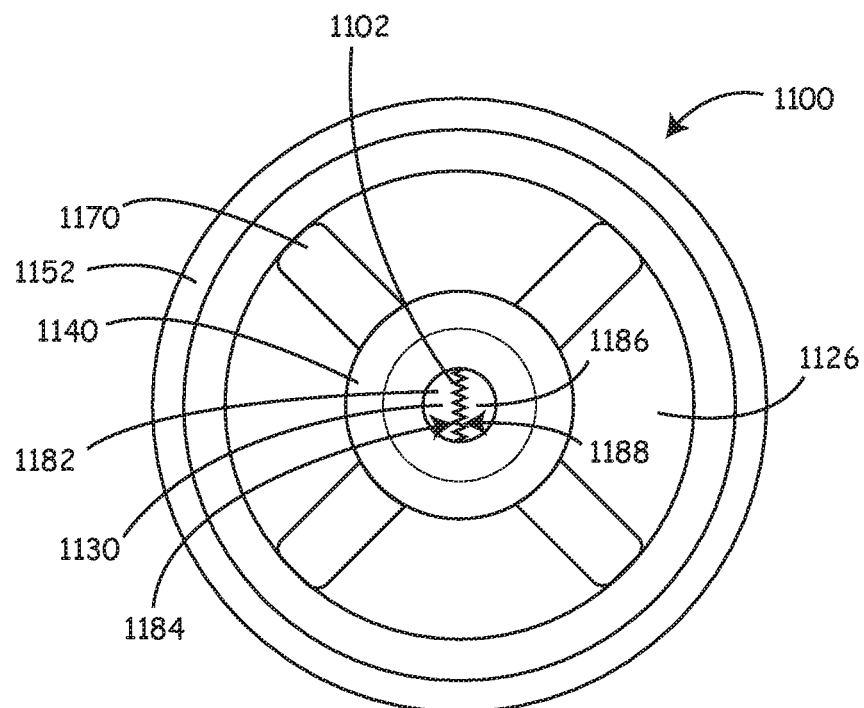
FIG. 11 is a plan view of the distal end of a hemostasis sealing device in accordance with various embodiments herein.

Referring now to FIG. 11, a plan view as taken from the distal end of a hemostasis sealing device 1100 is shown in accordance with various embodiments herein. In this view, the hemostasis sealing device 1100 can be seen to have a radial flange 1152, a tapered portion 1126, a barrel 1140, and support ribs 1170, with those elements being consistent with how they are described according to other embodiments herein. The hemostasis sealing device 1100 includes a second seal portion 1130. The second seal portion 1130 defines a first discrete portion 1182 and a second discrete portion 1186 separated from one another by a split line 1102 (or cut line or segmentation line) disposed along a split plane. The first discrete portion 1182 includes a mating surface 1184 and the second discrete portion 1186 also includes a mating surface 1188. The mating surfaces 1184 and 1188 can interface with each other when the second seal portion 1130 is in a closed configuration with nothing passing there through. The mating surfaces 1184, 1188 can have a surface topology including a plurality of raised portions and depressions. In this view, the surface topology is represented by a zig-zag line, but it will be appreciated that many other configurations are possible. The surface topology functions to reduce the surface area of the second seal portion 1130 contacting a medical device which is inserted through the second seal portion 1130. As such, the surface topology functions to reduce the amount of friction associated with inserting a medical device through the second seal portion.

In some embodiments, the split line (or cut line or segmentation line) may extend beyond the second seal portion. For example, the split line can also pass through adjoining structures such as the barrel. The surface topology does not have to be the same across the entirety of the split line. As such, in some embodiments the split line includes one or more zones with a first topology and one or more zones with a second topology that is different than the first topology. However, in other embodiments the surface topology is uniform across the entirety of the split line.

In yet other embodiments the second seal portion 1130 defines a first discrete portion 1182 and a second discrete portion 1186 wherein the first discrete portion 1182 and a second discrete portion 1186 can overlap to form an effective seal. The overlap can include, but is not limited to, a dovetail overlap such as the surface topologies described in FIG. 16.

Figure 12:
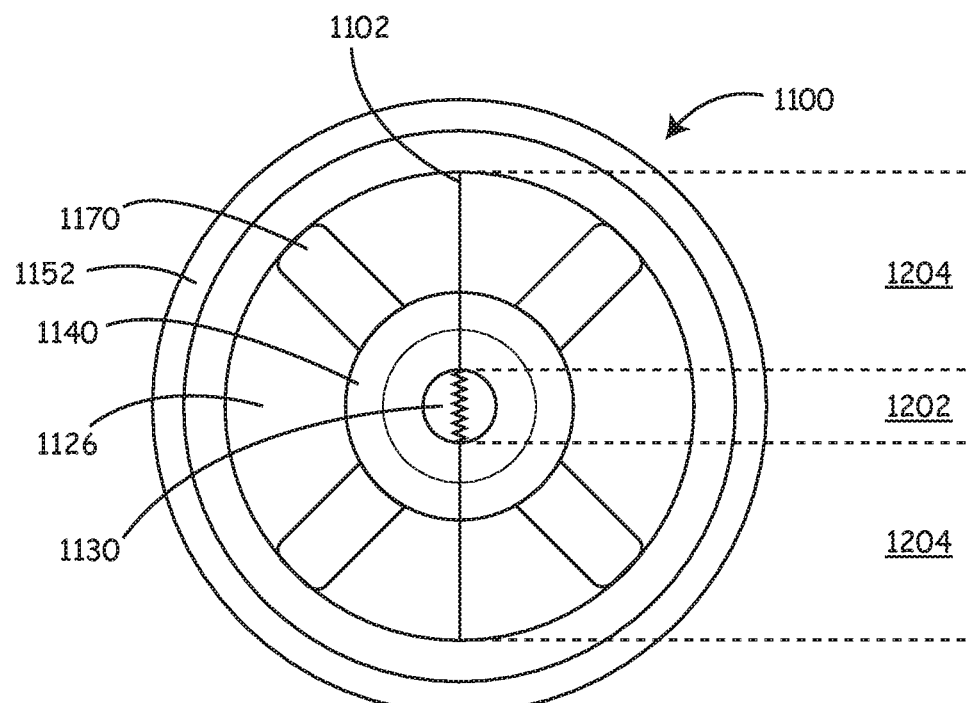
FIG. 12 is a plan view of the distal end of a hemostasis sealing device in accordance with various embodiments herein.

Referring now to FIG. 12, a plan view of the distal end of a hemostasis sealing device 1100 is shown in accordance with various embodiments herein. In this embodiment, the split line 1102 extends through the barrel 1140 and the tapered portion 1126. The split line 1102 includes outer split areas 1204 and an inner split area 1202. The split line 1102 can define a first surface topology in the area of the inner split area 1202 including raised portions and depressions. The split line 1102 can also define a different surface topology in the area of the outer split areas 1204. For example, the split line 1102 can simply have a surface topology that is substantially flat in the outer split areas 1204.

Figure 13:
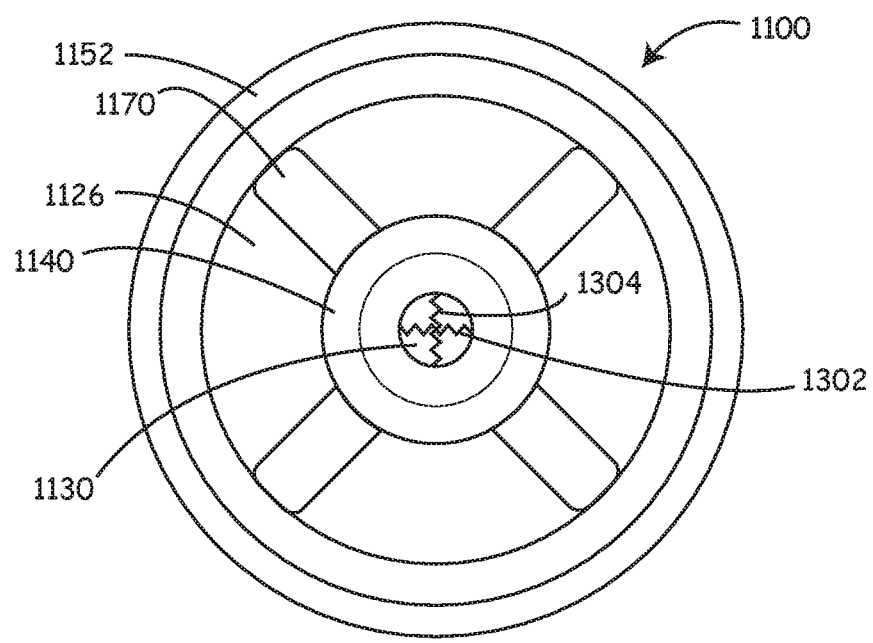
FIG. 13 is a plan view of the distal end of a hemostasis sealing device in accordance with various embodiments herein.

In some embodiments, hemostasis sealing devices herein can include multiple cut lines. Referring now to FIG. 13, a plan view of the distal end of a hemostasis sealing device 1100 is shown in accordance with various embodiments herein. In this view, the hemostasis sealing device 1100 includes a first split line 1302 and a second split line 1304. Thus, the second seal portion 1130 defines a four discrete portions, each with mating surfaces and a surface topology with raised portions and depressions. While first split line 1302 and second split line 1304 are shown substantially perpendicular to one another, they can also take on different angles with respect to one another.

Many different specific numbers of split lines and discrete portions of the second seal portion are contemplated herein. In various embodiments 1 to 10 split lines can be included forming 2 to 20 discrete portions of the second seal portion. Additionally, the multiple split lines can overlap forming an effective seal.

Figure 14:
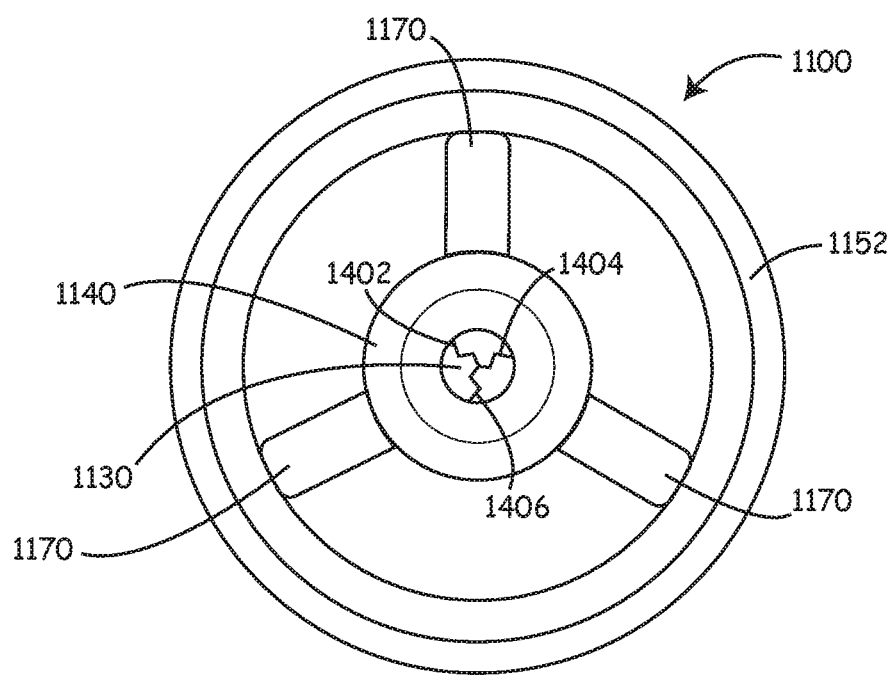
FIG. 14 is a plan view of the distal end of a hemostasis sealing device in accordance with various embodiments herein.

Referring now to FIG. 14, a plan view of the distal end of a hemostasis sealing device 1100 is shown in accordance with various embodiments herein. In this view, the hemostasis sealing device 1100 includes a first split line 1402, a second split line 1404, and a third split line 1406. Thus, the second seal portion 1130 defines a three discrete portions, each with mating surfaces and a surface topology with raised portions and depressions.

In various embodiments, one or more portions of the device can be covered by a hydrophilic layer of material in order to reduce friction associated with a medical device contacting such areas when it is inserted in the hemostasis sealing device.

Figure 15:
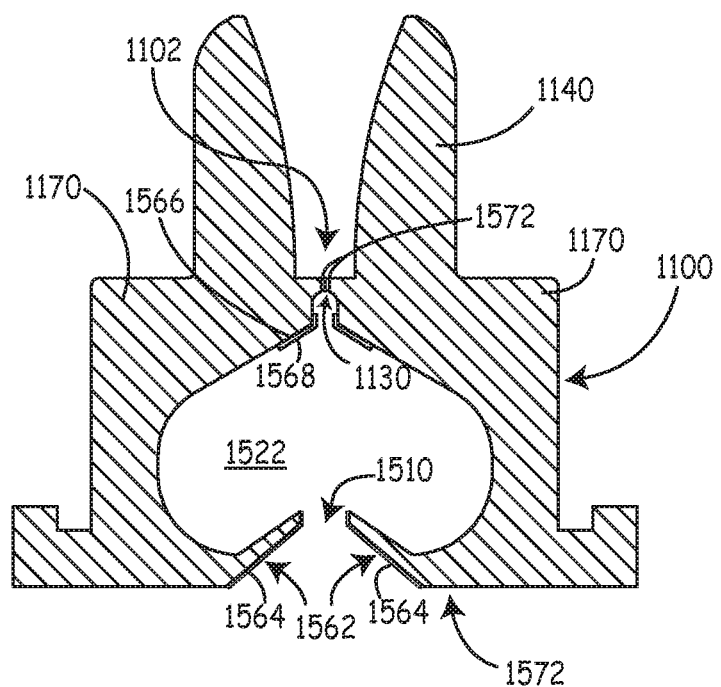
FIG. 15 is a cross-sectional view of a hemostasis sealing device in accordance with various embodiments herein.

Referring now to FIG. 15, a cross-sectional view of a hemostasis sealing device 1100 in accordance with various embodiments herein is shown. In FIG. 15, a first seal portion 1510 is shown near the proximal end 1572 of the hemostasis sealing device 1100. The first seal portion 1510 includes a sloped portion 1562 that is sloped toward the distal end, forming a frustoconical shape. The sloped portion 1562 includes an outer surface and a hydrophilic layer 1564 disposed on the outer surface. The hydrophilic layer 1564 can function to reduce the friction associated with inserting a device through the first seal portion 1510. The first seal portion 1510 can also take on shapes such as a distally facing bell shape, a distally facing pyramidal shape, and the like.

The hemostasis sealing device 1100 also includes a second seal portion 1130. In this view the split line 1102 dividing the second seal portion 1130 is shown on end and therefore the surface topology is not evident from this view. In some embodiments, the second seal portion 1130 includes hydrophilic layers 1572 disposed on the mating surfaces of the discrete portions of the second seal portion 1130. These hydrophilic layers 1572 can function to reduce the friction associated with inserting a device through the second seal portion 1130.

A device cavity 1522 is disposed inside the device 1100 between the first seal portion 1510 and a second seal portion 1130. In some embodiments, a hydrophilic layer 1568 is disposed on a sloped portion 1566 of the device lining the device cavity 1522 adjacent the second seal portion 1130. In some embodiments, a hydrophilic layer 1568 is disposed on all surfaces of the device facing the device cavity 1522.

It will be appreciated that many different surface topologies are contemplated herein for the mating surfaces of the discrete portions of the second seal portion. The surface topology can function to reduce the surface area in contact with medical devices inserted into one or more portions of the hemostasis sealing device The surface topology can include a plurality of raised portions and depressions. In some embodiments, the raised portions and depressions can include a regular pattern of peaks and valleys. The peaks and valleys can be consistent through at least a portion of the depth of the split line such that they form channels passing through the depth of the split line.

Figure 16:
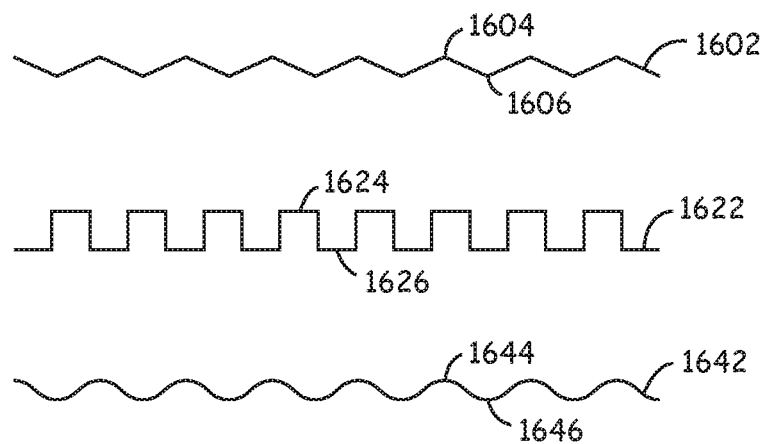
FIG. 16 is a view of exemplary surface topologies.

Referring to now to FIG. 16, a cross-sectional view is shown of some exemplary surface topologies. The first topology 1602 includes raised portions and depressions as a series of peaks 1604 and valleys 1606. The second topology 1622 includes raised portions and depressions as a series of flattened peaks 1624 and flattened valleys 1626. The third topology 1642 includes raised portions and depressions that are rounded.

Figure 17:
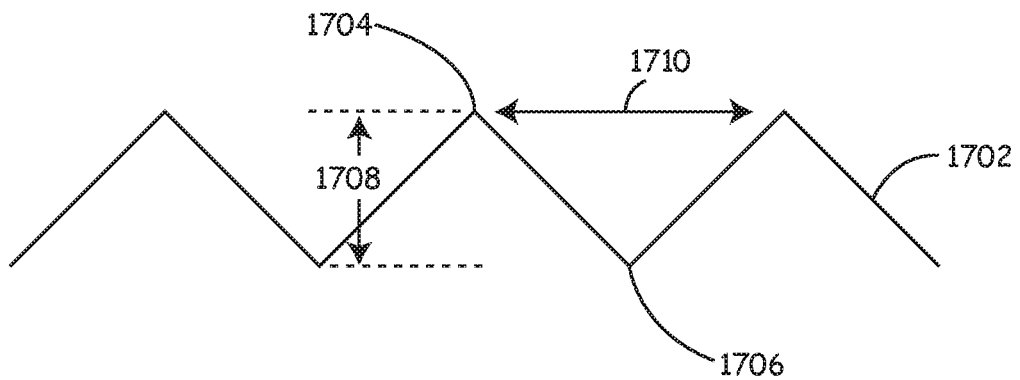
FIG. 17 is an illustration of an exemplary topology including exemplary peaks and valleys.

Referring now to FIG. 17, an illustration is shown of an exemplary topology 1702 including exemplary peaks 1704 and valleys 1706 in accordance with various embodiments herein. The peaks and valleys can have a pitch 1710 of about 0.01 mm to about 1.0 mm, in the absolute or on average. The vertical distance 1708 between the top of peaks 1704 and the bottom of valleys 1706 can be about 0.01 mm to about 1.0 mm, in the absolute or on average.

In various embodiments, a method of making a sealing device is included herein. The method can include obtaining an enclosure configured to at least partially receive a medical device, the enclosure defining a cavity and having a first seal portion and a second septum seal portion, the cavity disposed between the first seal portion and the second septum seal portion.

The method can further include forming a split in the second seal portion, the split defining discrete portions each comprising a mating surface to interface with mating surfaces of other discrete portions, the mating surface including a surface topology including a plurality of raised portions and depressions. It will be appreciated that there are various techniques that can be used to form the split.

Hydrophilic Layer Materials

As described above, in various embodiments a hydrophilic and/or lubricious layer of material can be disposed over one or more portions of the hemostasis sealing device. In some embodiments the hydrophilic layer of material can be arranged so as to contact any medical device that is inserted into the hemostasis sealing device, thereby reducing friction associated with the insertion of a medical device into the hemostasis sealing device.

Exemplary materials of the hydrophilic and/or lubricious layer can include, but are not limited to, lubricious low friction coating such as, a silicone oil, perfluorinated oils and waxes, optionally with covalent bonding, to decrease friction. These examples of low friction and hydrophilic coatings assist in increasing lubricity and decreasing the generation of particulate.

Examples of other fluorinated low friction coatings include coatings derived from water soluble fluoropolymers containing a UV-activatable group as described in U.S. Pat. No. 8,932,694 (to Rolfes et al.), the disclosure of which is incorporated herein by reference.

One class of hydrophilic polymers useful as polymeric materials for hydrophilic layers herein formation includes synthetic hydrophilic polymers. Synthetic hydrophilic polymers that are biostable (i.e., that show no appreciable degradation in vivo) are prepared from a suitable monomer including, but not limited to, acrylic monomers, vinyl monomers, ether monomers, or combinations of any one or more of these types of monomers. Acrylic monomers include, but are not limited to, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and one or more of derivatives or mixtures of any of these. Vinyl monomers include, but are not limited to, vinyl acetate, vinylpyrrolidone, vinyl alcohol, and derivatives of any of these. Ether monomers include, but are not limited to, ethylene oxide, propylene oxide, butylene oxide, and derivatives of any of these. Examples of polymers formed from these monomers include, but are not limited to, poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, but are not limited to, methyl vinyl ether/maleic anhydride copolymers and vinyl pyrrolidone/(meth)acrylamide copolymers. Further, mixtures of one or more or homopolymers or copolymers are used in some examples for hydrophilic layers.

Other hydrophilic polymer coatings for production of lubricious surfaces include, but are not limited to, poly(vinylpyrrolidone) layers with an acrylic acid polymer top coat. The acrylic acid polymer can be in direct contact with the poly(vinylpyrrolidone) layers. The direct contact can allow for hydrogen bonding interactions between the poly(vinylpyrrolidone) base coat and the acrylic acid polymer top coat. Exemplary lubricious coatings with poly(vinylpyrrolidone) base coat and an acrylic acid polymer top coat are described in U.S. Pat. App. Publn. 2016/0175489 (to Babcock et al.).

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

Other hydrophilic polymers used with the subject matter of this disclosure include derivatives of acrylamide polymers with photoreactive groups. One such representative hydrophilic polymer is the copolymerization of N-[3-(4-benzoylbenzamido)propyl] methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

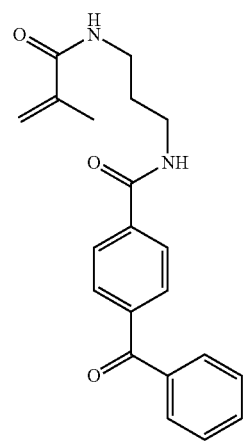

Formula I

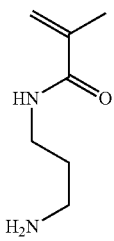

Formula II

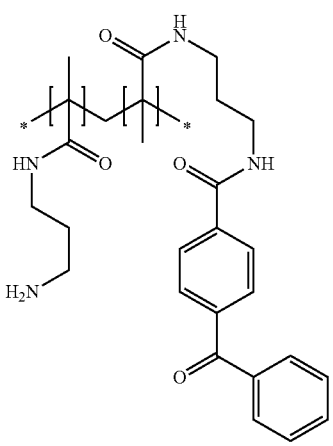

Formula III

In some embodiments, the hydrophilic polymer includes a vinyl pyrrolidone polymer, or a vinyl pyrrolidone/(meth) acrylamide copolymer such as poly(vinylpyrrolidone-co-methacrylamide). If a PVP copolymer is used, in some examples it includes a copolymer of vinylpyrrolidone and a monomer selected from the group of acrylamide monomers. Exemplary acrylamide monomers include (meth)acrylamide and (meth)acrylamide derivatives, such as alkyl (meth) acrylamide, as exemplified by dimethylacrylamide, and aminoalkyl (meth)acrylamide, as exemplified by aminopropyl-methacrylamide and dimethylaminopropylmethacrylamide. For example, poly(vinylpyrrolidone-co-N,N-dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075 (to Swan et al), the disclosure of which is incorporated herein by reference. Hydrophilic photo-polyacrylamide polymers such as poly(acrylamide-co-N-(3-(4-benzoylbenzamido)propyl) methacylamide), "Photo PA", and derivatives thereof can be used to form hydrophilic layers in exemplary embodiments of the present disclosure. Methods for the preparation of photo-polyacrylamide are described in U.S. Pat. No. 6,007,833 (to Chudzik et al.), the disclosure of which is incorporated herein by reference.

Other embodiments of hydrophilic layers include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl) methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic layers that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic layer can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methyl-propanesulfonate-co-N-(3-(4-benzoylbenzamido)propyl) methacrylamide)-co-methoxy poly(ethylene glycol) monomethacrylate. Other negatively charged species that can be incorporated into the hydrophilic layer are described in U.S. Pat. No. 4,973,493 (to Guire et al.), the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic layer are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat.

Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

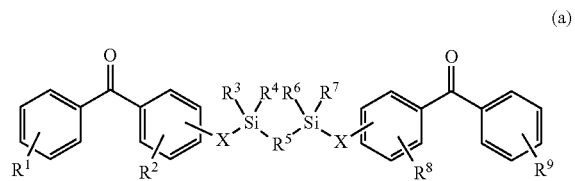

(a)

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

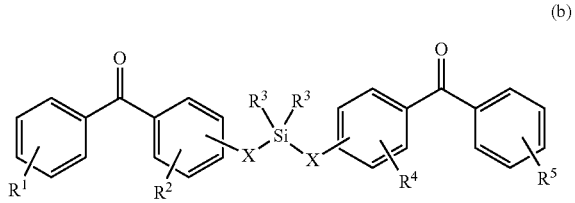

(b)

wherein R1 and R5 are any substitution; R2 and R4 can be any substitution, except OH; R3 can be alkyl, aryl, or a combination thereof; and X, independently, are O, N, Se, S, alkylene, or a combination thereof;

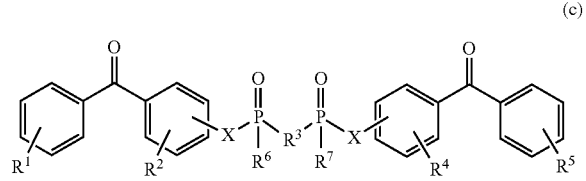

(c)

wherein R1, R2, R4 and R5 are any substitution; R3 is any substitution; R6 and R7 are alkyl, aryl, or a combination thereof; and each X can independently be O, N, Se, S, alkylene, or a combination thereof; and

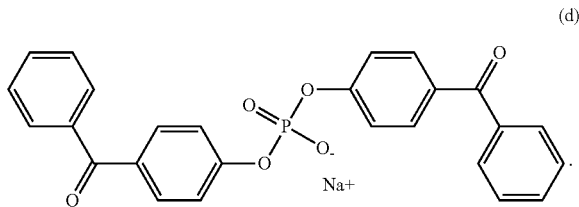

(d)

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y-X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018 (to Swan). The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition.

In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio) ethyl]-4-benzoylbenzylmethylammonium salt; 4,4-bis(4-benzoylbenzyl) morpholinium salt; ethylenebis[(2-(4-benzoylbenzyldimethylammonio)ethyl)-4-benzoylbenzylmethylammonium] salt; and 1,1,4,4-tetrakis(4-benzoylbenzyl) piperzinediium salt. See U.S. Pat. No. 5,714,360 (to Swan et al.). The counter ion is typically a carboxylate ion or a halide. On one embodiment, the halide is bromide.

In other embodiments, the ionic photoactivatable crosslinking agent can be a compound having the formula:

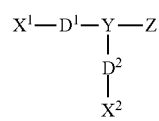

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

PG2-LE2-X-LE1-PG1 wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in Publ. No. U.S. 2012/0149934 (to Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Linking Agents"), the disclosure of which is incorporated herein by reference. Exemplary crosslinking agents can include non-ionic photoactivatable crosslinking agents having the general formula R1-X—R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Pat. No. 8,779,206 (to Guire et al.) U.S. Pat. No. 8,487,137 (to Guire et al.) and U.S. Pat. No. 7,772,393 (to Guire et al.) the content of all of which is herein incorporated by reference.

In some embodiments, crosslinking agents can include boron-containing linking agents including, but not limited to, the boron-containing linking agents disclosed in U.S. Pat. No. 9,410,044 (to Kurdyumov) the content of which is herein incorporated by reference. By way of example, linking agents can include borate, borazine, or boronate groups and coatings and devices that incorporate such linking agents, along with related methods. In an embodiment, the linking agent includes a compound having the structure (I):

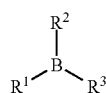

(I)

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B—R1, B—R2 and B—R3 can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic layer. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used to form the hydrophilic base layer. In yet other instances the tie layer can be added to the hydrophilic base layer. The tie layer can act to increase the adhesion of the hydrophilic base layer to the substrate. In other embodiments, the tie layer can act to increase adhesion of the hydrophobic active agent to the hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

In some embodiments of the present disclosure medicaments (e.g., bioactive agents) can be coated on devices herein. Additionally, excipients can be coated on devices herein to provide improved in vivo transfer characteristics of medicaments. Materials and devices for delivery of medicaments are described in U.S. Pat. Publications 2015/0140107 and 2012-0296274 (both to Slager), the content of both of which are herein incorporated by reference.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A device for vascular access hemostasis, the device comprising:
   an enclosure configured to at least partially receive a medical device, the enclosure defining a cavity and having
      a first seal portion; and
      a second seal portion, the cavity disposed between the first seal portion and the second seal portion;
      a barrel in structural communication with the second seal portion;
      the second seal portion comprising a septum seal;
   the second seal portion defining three or more discrete portions each separated from one another by one or more split lines, the discrete portions each comprising a mating surface configured to interface with mating surfaces of other discrete portions, the mating surface comprising a surface topology including a plurality of raised portions and depressions.

2. The device of claim 1, the first seal portion comprising an inwardly sloped portion, the inwardly sloped portion comprising an outer surface, further comprising a hydrophilic layer disposed on the outer surface.

3. The device of claim 2, the inwardly sloped portion forming a frustoconical shape.

4. The device of claim 1, further comprising a hydrophilic layer disposed on the mating surfaces of each discrete portion.

5. The device of claim 1, the raised portions and depressions comprising regular pattern of peaks and valleys.

6. The device of claim 1, the peaks and valleys having a pitch of about 0.01 mm to about 1.0 mm.

7. The device of claim 1, a vertical distance between the top of peaks and the bottom of valleys comprising about 0.01 mm to about 1.0 mm.

8. The device of claim 1, wherein the one or more splits have a depth sufficient to pass through the barrel and the septum seal, but not through the entire enclosure.

9. The device of claim 1, further comprising support ribs operably connected to the second seal portion, wherein the support ribs are configured for compressive interfacing with a housing.

10. The device of claim 1, wherein the first seal portion comprises a hole seal.

11. The device of claim 1, wherein the first seal portion comprises a ring seal.

12. The device of claim 1, wherein the second seal portion is configured to be held in compression by a mating housing.

13. The device of claim 1, wherein the mating surface comprises a portion having the surface topology including the plurality of raised portions and depressions and comprising a portion that is substantially flat.

14. A sealing device comprising:
   a device enclosure defining a cavity, wherein the device enclosure is configured to compressively interface with a housing;
   a first seal portion in communication with the device enclosure, the first seal portion defining an opening; and
   a second seal portion in communication with the device enclosure; and
   the second seal portion defining three or more discrete portions separated from one another by a split along a split plane, the discrete portions each comprising a mating surface to interface with mating surfaces of other discrete portions, the mating surface comprising a surface topology including a plurality of raised portions and depressions.

15. The sealing device of claim 14, the device enclosure comprising a plurality of support ribs in compressive communication with the second seal portion.

16. The sealing device of claim 14, wherein the support ribs are offset from the split by about 45 degrees.

17. The sealing device of claim 14, wherein the support ribs are substantially symmetrical relative to the split.

18. A method of making a sealing device comprising:
   obtaining an enclosure configured to at least partially receive a medical device, the enclosure defining a cavity and having
      a first seal portion; and
      a second septum seal portion, the cavity disposed between the first seal portion and the second septum seal portion; and
   forming a split in the second seal portion, the split defining three or more discrete portions each comprising a mating surface to interface with mating surfaces of other discrete portions, the mating surface comprising a surface topology including a plurality of raised portions and depressions.

* * * * *